US006377656B1

(12) United States Patent
Ueki et al.

(10) Patent No.: US 6,377,656 B1
(45) Date of Patent: Apr. 23, 2002

(54) X-RAY CONTROL METHOD AND X-RAY APPARATUS

(75) Inventors: Hironori Ueki, Kokubunji; Ken Ueda, Oume; Akira Kuba, Nagareyama, all of (JP)

(73) Assignee: Hitachi Medical Corporation, Tokyo (JP)

(*) Notice: Subject to any disclaimer, the term of this patent is extended or adjusted under 35 U.S.C. 154(b) by 0 days.

(21) Appl. No.: 09/423,241

(22) PCT Filed: May 1, 1998

(86) PCT No.: PCT/JP98/02003

§ 371 Date: Nov. 5, 1999

§ 102(e) Date: Nov. 5, 1999

(87) PCT Pub. No.: WO98/52388

PCT Pub. Date: Nov. 19, 1998

(30) Foreign Application Priority Data

May 9, 1997 (JP) .............................................. 9-119102

(51) Int. Cl.⁷ ................................................. H05G 1/64
(52) U.S. Cl. ....................................................... 378/98.7
(58) Field of Search ................................ 378/98.7, 108, 378/97

(56) References Cited

U.S. PATENT DOCUMENTS 4,955,043 A * 9/1990 Nekovar .................... 378/98.7

FOREIGN PATENT DOCUMENTS

JP          A-57-88698          6/1982

OTHER PUBLICATIONS

SPIE vol. 2432, pp. 216–227, "Large Area, Flat–Panel, Amorphous Silicon Imagers".

* cited by examiner

Primary Examiner—Craig E. Church
(74) Attorney, Agent, or Firm—Antonelli, Terry, Stout & Kraus, LLP

(57) ABSTRACT

An X-ray apparatus in which a mean value of a weighted histogram obtained by multiplying a histogram of numbers of data corresponding to image intensities in a reference image which is an X-ray image picked up in an X-ray fluoroscopy mode and a weighting function whose variable depends on the image intensities is arithmetically determined for controlling an output power of an X-ray tube so that the mean value of the integrated histogram approaches a predetermined value.

33 Claims, 9 Drawing Sheets

FIG. 10

TABLE 300

301 — CAMERA MODE

| | 500 | 1000 | 2000 |
|---|---|---|---|
| $F_C$ | | | |

302 — I.I. MODE

| | 7" | 9" | 12" |
|---|---|---|---|
| $F_I$ | | | |

303 —

GRID 1, FILTER 3

GRID 1, FILTER 2

GRID 1, FILTER 1
$a_p = \_, b_p = \_, c_p = \_ \quad k_F = \_, V_F = \_$
$a_m = \_, b_m = \_, c_m = \_ \quad k_L = \_, V_L = \_$

X-RAY CONTROL METHOD AND X-RAY APPARATUS

TECHNICAL FIELD

The present invention relates to an X-ray apparatus and more particularly relates to techniques which can effectively be applied to exposure control for controlling properly or pertinently the conditions for generating X-rays in a fluoroscopy as well as in a radiography for X-ray diagnosis.

BACKGROUND ART

In the conventional X-ray fluoroscopy/radiography system, the automatic X-ray exposure apparatus is so designed as to pick up a portion of output light of an X-ray image intensifier or X-ray I.I. for detection by means of a photomultiplier or the like to thereby effect X-ray fluoroscopy and radiography controls on the basis of the detection signal. By way of example, for the X-ray fluoroscopy control, a feedback control is performed for a tube current and a tube voltage of an X-ray tube or aperture of an optical stop or iris so that an integral value of the detection signal outputted from the photomultiplier per unit time can assume a constant value, whereby brightness of the X-ray fluoroscopic image is constantly held at a pertinent level or value. Further, in the X-ray radiography control, X-rays are interrupted at a time point when the integral value of the detection signal outputted from the photomultiplier has attained a predetermined value, to thereby render available the X-ray radiographic image of proper brightness (phototimer).

As another example of the automatic X-ray exposure control method, there can be mentioned an automatic X-ray exposure apparatus described in Japanese Patent laid-open Publication JP-A-57-88698. In this automatic X-ray exposure apparatus, a plurality of photodiodes are employed for detecting output light of the X-ray I.I. in place of the photomultiplier mentioned above, wherein the X-ray fluoroscopy and radiography control is carried out on the basis of outputs of several photodiodes selected from the plural photodiodes.

In the automatic X-ray exposure control apparatus in which the photomultiplier is employed, as described above, a portion of the output light of the X-ray I.I. is picked up by the photomultiplier by way of a half mirror. Consequently, the amount of light inputted to a television camera will decrease, giving rise to a problem that light utilization efficiency is degraded. Besides, because the light pick-up field is disposed at only one location in the vicinity of the X-ray I.I., difficulty is encountered in effecting the control so that the image having proper or desirable brightness as a whole can be ensured for the X-ray images exhibiting various X-ray absorption dose distributions.

On the other hand, in the automatic X-ray exposure control apparatus described in Japanese Patent laid-open Publication JP-A-57-88698, the light pick-up field can be enlarged by disposing a plurality of photodiodes in place of the photomultiplier. However, the number of photodiodes is ordinarily in a range of eight to twelve or so. Consequently, in the case where one or more photodiodes are positioned near to a boundary between the X-rays transmitted through an object under inspection and the directly incident X-rays, a slight movement of the object under inspection will bring about significant variation in the amount of X-rays impinging onto these photodiodes, incurring a problem that the tone of the displayed image undergo remarkable variation.

As a method of coping with the problems described above, there has been proposed a method of performing the X-ray fluoroscopy/radiography control for an object under inspection by using directly a video signal outputted from a television camera.

However, this method suffers problems described below and thus encounters difficulty in realization for practical applications.

By way of example, because the dynamic range of the television camera is very narrow when compared with that of the photomultiplier and the photodiode array, halation will take place as the amount of light increases, making it impossible to detect accurately the X-ray output, to a disadvantage. Furthermore, in the X-ray radiography control, the time taken for controlling the generation of X-rays is short when compared with a time taken for frame reading of the television camera, involving thus another problem. Additionally, control algorithm for ensuring proper brightness for the fluoroscopic image as well as the radiographic image of a concerned part as required for diagnosis is not definite, bringing about a further problem.

DISCLOSURE OF INVENTION

An object of the present invention is to provide an X-ray control method and an X-ray apparatus which make it possible to perform the X-ray fluoroscopy/radiography control more pertinently or properly when compared with the conventional techniques in the X-ray fluoroscopy/radiography control in which a video signal is employed.

Another object of the present invention is to provide an X-ray control method and an X-ray apparatus which can ensure enhanced diagnosis performance for inspectors.

For achieving the objects mentioned above, in the X-ray apparatus according to the present invention, a fluoroscopic image in an X-ray fluoroscopy or an X-ray image picked up in a preliminary radiography is used as a reference image for determining a histogram representing a distribution of numbers of data corresponding to image intensities (pixel values) of the reference image. On the other hand, a weighting function having a variable dependent on the image intensities is determined in order to extract properly the image data. In succession, the weighting function and the histogram are multiplied to thereby determine a weighted histogram, and then output power of an X-ray tube is so controlled that a mean value of the weighted histogram assumes a predetermined value.

Describing briefly the effects achieved by typical embodiments of the invention disclosed in the present application, they are as follows:

(1) In the X-ray fluoroscopy/radiography control for which the video signal is made use of, the X-ray fluoroscopy/radiography control can be carried out more properly when compared with the conventional technique.

(2) With the X-ray fluoroscopy/radiography control in which the video signal is made use of, diagnostic performance can be enhanced.

(3) Because the X-ray apparatus can be implemented in a simplified structure, there can be provided an X-ray diagnosis system of low cost.

(4) The X-ray fluoroscopy can be realized in a stabilized manner.

(5) Sensitive reaction of the sensor in response to movement of an object under inspection can be suppressed.

BRIEF DESCRIPTION OF DRAWINGS

FIG. 10 is a view for illustrating a data structure of a table according to the instant embodiment of the invention.

BEST MODES FOR CARRYING OUT THE INVENTION

In the following, the present invention will be described in detail in conjunction with an exemplary embodiment thereof by reference to the drawings.

By the way, throughout all the views illustrating the exemplary embodiment of the invention, components serving for same function are designated by like reference symbols and repeated description thereof will be omitted.

Figure 1:
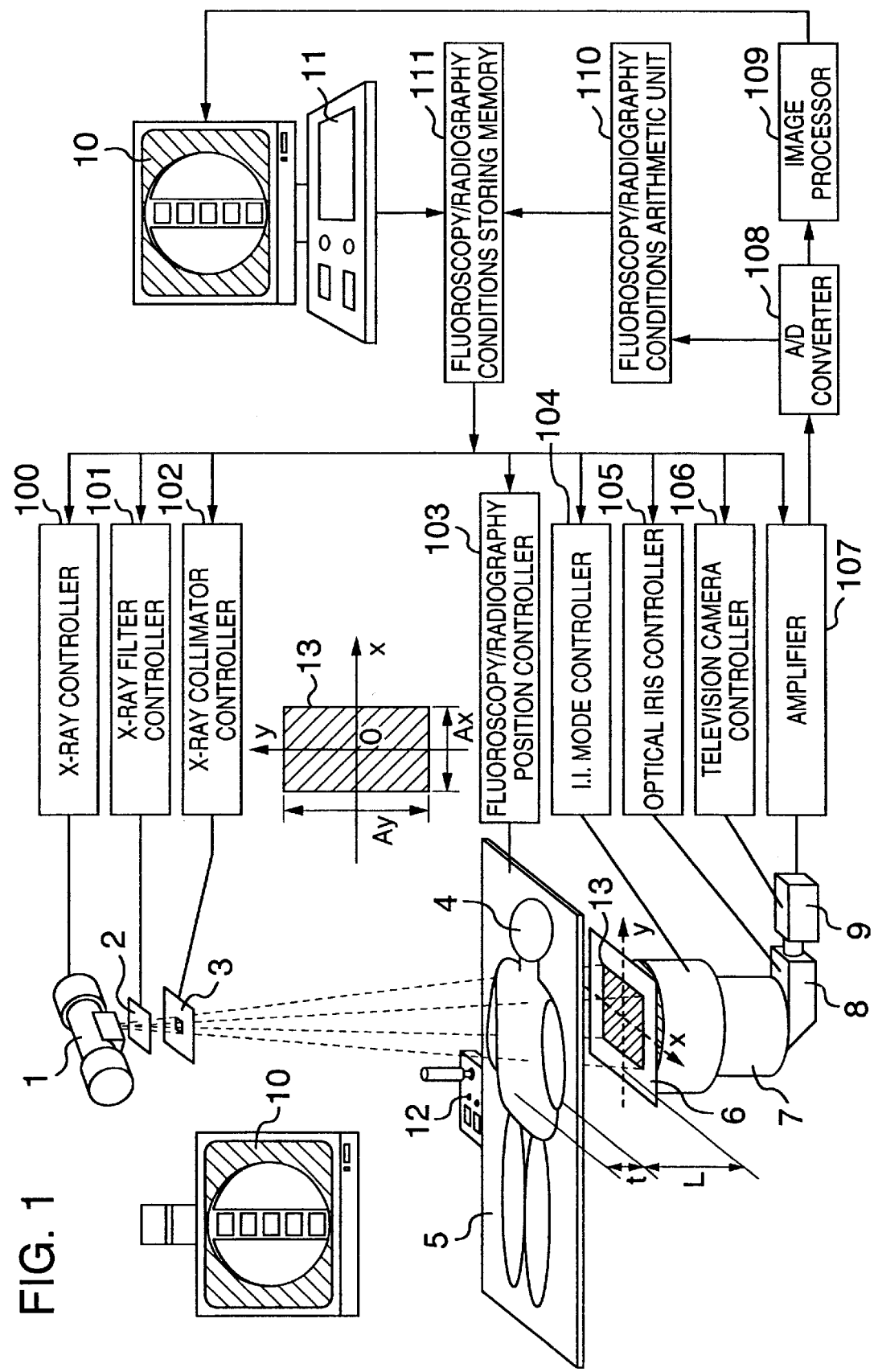
FIG. 1 is a block diagram showing schematically a structure of an X-ray apparatus according to an exemplary embodiment of the present invention.

FIG. 1 is a block diagram showing schematically a structure of an X-ray apparatus according to an exemplary embodiment of the present invention. The X-ray apparatus (X-ray fluoroscopy/radiography apparatus) according to the instant embodiment of the invention is comprised of an X-ray tube 1, an X-ray filter 2, an X-ray collimator (X-ray irradiation field limiting means) 3, a bed top board 5, an X-ray grid 6, an X-ray image intensifier (hereinafter referred to as the X-ray I.I.) 7, an optical lens system 8, a television camera 9, a monitor 10, a remote control/manipulation console 11, a control/manipulation console 12, an X-ray controller 100, an X-ray filter controller 101, an X-ray collimator controller 102, a fluoroscopy/radiography position controller 103, an I.I. mode controller 104, an optical stop or iris controller 105, a television camera controller 106, an amplifier 107, an analogue-to-digital or A/D converter 108, an image processor 109, a fluoroscopy/radiography conditions arithmetic unit 110 and a fluoroscopy/radiography conditions storing memory 111. Further, in FIG. 1, reference numeral 4 denotes an object under inspection and 13 denotes an X-ray irradiation field in X-ray fluoroscopy/radiography modes of the X-ray fluoroscopy/radiography apparatus according to the instant embodiment of the invention.

In the case of the instant embodiment, an imaging means is constituted by the X-ray I.I. 7, the optical lens system 8 and the television camera 9. Further, an imaging system is constituted by the X-ray tube 1, the X-ray filter 2, the X-ray collimator 3, the X-ray grid 6 and the imaging means.

Referring to FIG. 1, distance between the X-ray tube 1 and an input plane of the X-ray I.I. 7 is, for example, 120 cm, the thickness of the object 4 under inspection is represented by t and distance between a top plane of the bed top board 5 and the input plane of the X-ray I.I. 7 (hereinafter, this distance will be referred to as the air gap) is represented by L. The thickness t of the object 4 under inspection changes variously in dependence on individual difference or posture of the object 4 under inspection. Further, the air gap L changes in dependence on the position setting of the bed top board 5. The diameter of the X-ray input face or plane of the X-ray I.I. 7 is 30.48 cm. An x,y-coordinate system is defined on the input plane of the X-ray I.I. 7 as an orthogonal coordinate system having the origin at a center of the X-ray I.I., wherein the longitudinal direction is defined as the y-axis with the direction orthogonal to the y-axis being defined as the x-axis. The X-ray grid 6 is secured fixedly on the input plane of the X-ray I.I. 7. In the television camera 9, a high-resolution CCD array is used as the image pick-up device.

Next, description will be made briefly of components or units of the x-ray fluoroscopy/radiography apparatus shown in FIG. 1.

The X-ray controller 100 serves as a control unit for reading a tube voltage value and a tube current value from the fluoroscopy/radiography conditions storing memory 111 upon X-ray fluoroscopy and radiography to thereby control generation of the X-rays from the X-ray tube 1 on the basis of the values as fetched.

The X-ray filter controller 101 serves as a control unit for reading species and presence/absence of the X-ray filter 2 from the fluoroscopy/radiography conditions storing memory 111 in the X-ray fluoroscopy/radiography modes to thereby perform corresponding controls. The X-ray filter 2 serves for changing energy distribution of the X-rays radiated from the X-ray tube 1.

The X-ray collimator controller 102 is a control unit for controlling a position of the X-ray collimator 3 for setting the X-ray irradiation field 13 upon X-ray fluoroscopy/radiography by reading the position data from the fluoroscopy/radiography conditions storing memory 111. In this conjunction, the X-ray irradiation field 13 is defined as an irradiation field of the X-rays on the input face or plane of the X-ray I.I. 7, as mentioned previously, wherein extents or dimensions of the X-ray irradiation field in the x-axis direction and the y-axis direction are represented by Ax and Ay, respectively.

The fluoroscopy/radiography position controller 103 is a control unit for controlling the position of the object 4 under inspection in the X-ray fluoroscopy/radiography.

The I.I. mode controller 104 is a control unit for controlling the I.I. mode of the X-ray I.I. 7 in the X-ray fluoroscopy/radiography on the basis of values read from the fluoroscopy/radiography conditions storing memory 111, wherein the I.I. mode in turn prescribes the X-ray detecting region of the X-ray I.I. 7.

The optical iris controller 105 is a control unit for controlling optical iris aperture area of the optical lens system 8 in the X-ray fluoroscopy/radiography on the basis of values read from the fluoroscopy/radiography conditions storing memory 111.

The television camera controller 106 is a unit for controlling scanning conditions (hereinafter referred to as the camera mode) of the television camera 9 in the X-ray fluoroscopy/radiography on the basis of values read from the fluoroscopy/radiography conditions storing memory 111.

Furthermore, the television camera controller 106 serves for controlling the scan timing of the television camera 9.

The amplifier 107 serves for amplifying the output signal of the television camera 9 in the X-ray fluoroscopy/radiography, wherein the amplified signal outputted from the amplifier 107 is inputted to the A/D converter 108. In the case of the instant embodiment of the invention, gain (amplification factor, gain) of the amplifier is determined on the basis of the value read from the fluoroscopy/radiography conditions storing memory 111.

The A/D converter 108 serves for converting the output signal of the television camera 9 undergone the gain adjustment by the amplifier 107 into a digital signal. The quantization bit number for the A/D conversion is e.g. 12 bits. In that case, pixel values (image intensities) of the digital image are expressed by numerical values in a range of "0 (zero)" to "4095".

The image processor 109 is a unit designed for performing image processing known per se on the digital image outputted from the A/D converter 108, to thereby output the digital image obtained after the image processing to the monitor 10, wherein the digital image as outputted is displayed in the monitor 10.

The fluoroscopy/radiography conditions arithmetic unit 110 is an arithmetic unit for arithmetically determining proper values of the tube voltage and the tube current, respectively, of the X-ray tube 1 in the fluoroscopy mode on the basis of the digital image outputted from the A/D converter 108, wherein the results of the arithmetic operation is saved in the fluoroscopy/radiography conditions storing memory 111. Further, the fluoroscopy/radiography conditions arithmetic unit 110 is designed to arithmetically determine the image pick-up time in the radiography mode, the result of which is saved in the fluoroscopy/radiography conditions storing memory 111 as well.

Next, description will be directed to operation of the X-ray fluoroscopy/radiography apparatus according to the instant embodiment of the invention by reference to FIG. 1. In the description which follows, it is resumed that the tube voltage V and/or the tube current quantity Q of the X-ray tube 1 (wherein the tube current quantity Q is defined as a product of the tube current of the X-ray tube 1 and a time taken for reading one frame of the television camera 9 in the X-ray fluoroscopy while in the X-ray radiography, the tube current quantity Q is defined as a product of the tube current of the X-ray tube 1 and the time taken for the radiography, both products being expressed in so-called mAs values), the species of the X-ray filter 2, the values Ax and Ay defining the X-ray irradiation field 13, the air gap L, the type of the X-ray grid 6, the I.I. mode, the optical iris aperture area Ω, the camera mode and the gain G of the amplifier 107 are employed as parameters, respectively, wherein the set values of the above-mentioned individual parameters in the X-ray fluoroscopy and the X-ray radiography are used as the X-ray fluoroscopy conditions and the X-ray radiography conditions, respectively. The person in charge of inspection or inspector can set a concerned part destined for fluoroscopy/radiography (e.g. chest, abdomen, etc.) of an object under inspection through the medium of the remote control/manipulation console 11 or the control/manipulation console 12. In that case, the values as set are also added to the X-ray fluoroscopy conditions and the X-ray radiography conditions as parameters. The X-ray fluoroscopy conditions and the X-ray radiography conditions are saved in the fluoroscopy/radiography conditions storing memory In the X-ray fluoroscopy as well as the X-ray radiography, energy distribution of the X-rays emitted from the X-ray tube 1 is first changed by the X-ray filter 2, whereon the X-ray irradiation field 13 is restricted by the X-ray collimator 3. Thereafter, the X-rays transmit through the object 4 under inspection. At that time, a portion of the X rays is scattered by the object 4 under inspection upon transmitting therethrough. A major proportion of the scattered X-rays is cut off by the X-ray grid 6. However, another part of the scattered X-rays may transmit through the X-ray grid 6 without being cut off. The scattered X-rays transmitted through the X-ray grid 6 and the direct X-rays transmitted through the object 4 under inspection without being scattered are detected concurrently by the X-ray I.I. 7 to be thereby converted into an optical image. The optical image is then focused at the television camera 9 after the amount of light has been regulated by means of the optical stop or iris of the optical lens system 8. The television camera 9 converts the above-mentioned optical image into a video signal (analogue image) which is outputted from the television camera. The video signal outputted from the television camera 9 is adjusted in respect to the signal intensity by the amplifier 107, and then converted into a digital signal (digital image) from the analogue signal by the A/D converter 108. The video signal converted into the digital signal, i.e., the digital image, is outputted to the monitor 10 after having undergone predetermined image processings by the image processor 109, to be thereby displayed on the display screen of the monitor 10.

At that time, in the X-ray fluoroscopy mode, the digital image outputted from the A/D converter 108 is supplied to the image processor and at the same time to the fluoroscopy/radiography conditions arithmetic unit 110. The fluoroscopy/radiography conditions arithmetic unit 110 in turn determines arithmetically the values of the tube voltage V and the tube current quantity Q of the X-ray tube 1 for the fluoroscopy, the optical iris aperture area Ω and the gain G of the amplifier 107, respectively, on a real time basis in accordance with a procedure described hereinafter so that the digital image inputted has proper values. The results of the arithmetic operations mentioned above are overwritten at the storage locations for the relevant values, respectively, in the fluoroscopy/radiography conditions storing memory 111. Thus, the fluoroscopy/radiography conditions storing memory 111 holds the value of the tube voltage V and the tube current quantity Q of the X-ray tube 1 for the fluoroscopy which are inputted from the fluoroscopy/radiography conditions arithmetic unit 110, the optical iris aperture area Ω and the gain G of the amplifier 107 as inputted together with the information concerning the camera mode, the I.I. mode, the X-ray irradiation field Ax; Ay, setting of a concerned part of the object under inspection, the type of the X-ray filter, the type of the X-ray grid and the set value of the air gap L inputted by the inspector through the medium of the remote control/manipulation console 11 or the control/manipulation console 12. The X-ray controller 100, the optical iris controller 105 and the amplifier 107 control on the real time basis the X-ray tube voltage and the X-ray tube current quantity, the optical iris aperture and the amplifier gain in accordance with the respective relevant information, the results of which are reflected onto the video signal intensity to be thereby fed back to the fluoroscopy/radiography conditions arithmetic unit 110 after having undergone the A/D conversion. By virtue of the arithmetic operations and the control (feedback control) based on the results of the arithmetic operations as described above, the control for generating the pertinent or proper display image in the X-ray fluoroscopy mode is performed.

On the other hand, in the X-ray fluoroscopy mode, the inspector or operator performs alignment of position (fluoroscopy/radiography position) through the medium of the remote control/manipulation console 11 or the control/manipulation console 12 so that the concerned part to be observed of the object 4 under inspection is located at a pertinent position on the display screen of the monitor 10. At the time point the positional alignment has been accomplished, an X-ray radiography start command is inputted through the remote control/manipulation console 11 or the control/manipulation console 12, whereby a start signal for the X-ray radiography is generated. Upon generation of the signal commanding the start of the X-ray radiography, a preliminary X-ray radiography and an intrinsic X-ray radiography are carried out in accordance with procedures described below.

In the preliminary X-ray radiography mode, the X-ray controller 100 responds to generation of the radiography start signal to thereby stop the generation of the X-rays, whereby the X-ray fluoroscopy is terminated. In succession, the X-ray controller 100, the X-ray collimator 102, the I.I. mode controller 104 and the television camera controller 106 read out from the fluoroscopy/radiography conditions storing memory 111 the preset values of the tube voltage V' of the X-ray tube 1, the X-ray irradiation field parameters A'x and A'y, the preset values of the I.I. mode and the camera mode, respectively, for the intrinsic X-ray radiography, to thereby validate the respective values. At this juncture, the tube voltage V' of the X-ray tube 1 for the intrinsic X-ray radiography is determined on the basis of the tube voltage V at the time of termination of the fluoroscopy, wherein relation between the tube voltages V and V' mentioned above is previously set through the medium of the remote control/manipulation console 11. Further, the set values for the X-ray irradiation field A'x; A'y, the I.I. mode and the camera mode for the intrinsic X-ray radiography are set previously by the inspector through the remote control/manipulation console 11 or the control/manipulation console 12. Further, the X-ray controller 100 sets the current value of the X-ray tube 1 to kQ for the tube current value Q at the end of the fluoroscopy, wherein k represents a value set previously through the medium of the remote control/manipulation console 11 and is set ordinarily at a value of 0.1 or so. The reason why k is set to a relatively small value is to prevent occurrence of halation in the preliminary X-ray radiography. Simultaneously with completion of all the settings mentioned above, the X-ray controller 100 sends an X-ray generation signal to the X-ray tube 1 for thereby carrying out the preliminary X-ray radiography.

Upon completion of the preliminary X-ray radiography, the fluoroscopy/radiography conditions arithmetic unit 110 reads out through the A/D converter 108 the preliminary radiographic image undergone the A/D conversion and determines arithmetically the tube current quantity Q', the optical iris aperture area Ω' and the gain G' for the intrinsic X-ray radiography, which is then followed by writing the results of the arithmetic operations in the fluoroscopy/radiography conditions storing memory 111. Subsequently, the X-ray controller 100, the optical iris controller 105 and the amplifier 107 read out from the fluoroscopy/radiography conditions storing memory 111 the tube current quantity Q', the optical iris aperture area Ω' and the gain G', respectively, for the intrinsic X-ray radiography for setting thereof. Upon completion of setting of these values, the X-ray controller 100 sends then the X-ray generation signal to the X-ray tube 1 to thereby allow the intrinsic X-ray radiography to be carried out. The picked-up X-ray image is stored in a frame memory not shown after having been converted into a digital signal through the A/D converter 108.

Relations between the X-ray fluoroscopy conditions and the X-ray radiography conditions on one hand and the X-ray image output on the other hand may be given by an approximate expression disclosed in Japanese Patent Application No. 267518/1996 (JP-A-8-267518) filed by the same applicant as the present application. According to the teachings disclosed in the above publication, when a mean pixel value in the vicinity of the center of the output image from the A/D converter 108 is represented by I, then I can be approximated by the undermentioned expression 1.

According to the present invention, the expression 1 is used for estimating a halation level.

$$I = Q \ \Omega G F_C F_I P(V) e^{-\mu(V)t} f_A(t, V, A_x, A_y) f_L(t, V, L)$$

$$P(V) = a_p V^2 + b_p V + c_p$$

$$\mu(V) = a_m V^2 + b_m V + c_m$$

$$f_A(t, V, A_x, A_y) = 1 - t k_F (V - V_F)(2A_o - A_x - A_y)$$

$$f_L(t, V, L) = 1 - t k_L (V - V_L)(L - L_o) \qquad \text{[Expression 1]}$$

In the above expressions, $F_C$ and $F_I$ represent proportional coefficients which are determined for every camera mode and I.I. mode, respectively. Further, P(V) represents a direct X-ray output function in the case no object is present for inspection, and $\mu(V)$ represents an X-ray absorption coefficient function in the case where the object 4 under inspection is approximated by a plate or board of an acrylic resin or the like. The direct X-ray output function P(V) and the X-ray absorption coefficient function $\mu(V)$ can be approximated by quadratic functions of the tube voltage V, respectively, wherein values of $a_p$, $b_p$ and $c_p$ and values of $a_m$, $b_m$ and $c_m$ represent coefficients in the functions P(V) and $\mu(V)$, respectively. Furthermore, $f_A$ represents a function for correcting variation of the scattered X-ray dose which accompanies change of the X-ray irradiation field. In the function $f_A$, the value of $A_o$ represents a standard value of the X-ray irradiation field. Further, $k_F$ and $V_F$ represent constants, respectively. Additionally, $f_L$ represents a function for correcting variation in the amount or dose of scattered X-rays brought about by change of the air gap. The value of $L_o$ in the function $f_L$ represents a standard value of the air gap.

Further, $k_L$ and $V_L$ represent constants, respectively. Values of $a_p$, $b_p$, $c_p$, $a_m$, $b_m$, $c_m$, $k_F$, $V_F$, $k_L$ and $V_L$ represent characteristic values determined in dependence on the configuration of the X-ray fluoroscopy/radiography system, the type of the X-ray filter and the species of the X-ray I.I., as employed, respectively. As will be described later on, in order to allow the expression 1 to be used for the arithmetic operations by the fluoroscopy/radiography conditions arithmetic unit, the values of $F_C$ and $F_I$ as well as the characteristic values are held in a memory, for example, in the form of a table.

Figure 2:
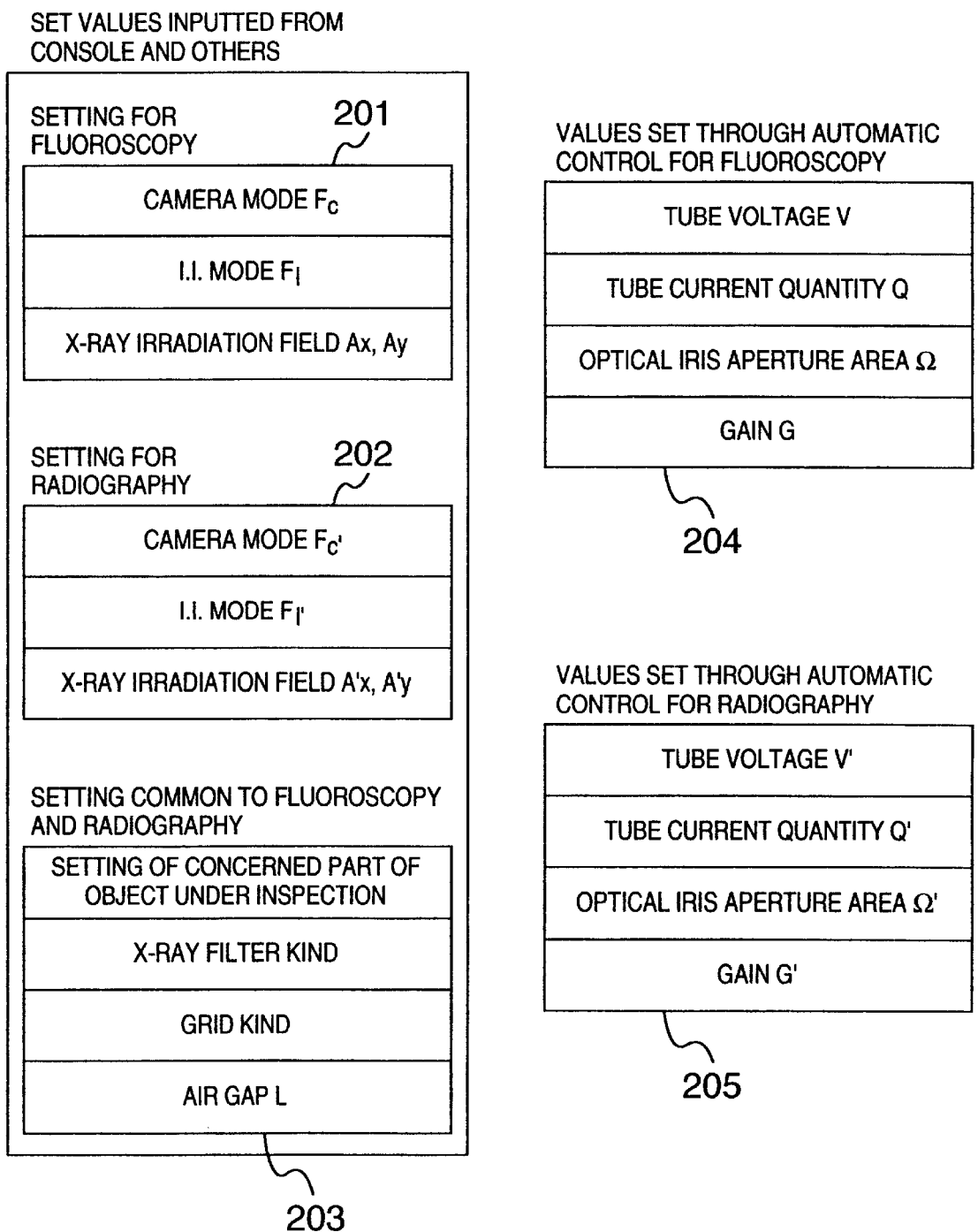
FIG. 2 is a view for illustrating, by way of example, settings of parameters for X-ray fluoroscopy and X-ray radiography.

FIG. 2 shows views for illustrating, by way of example, settings of parameters for the X-ray fluoroscopy and the X-ray radiography, respectively. In the following, description will be made of typical example of the individual parameter setting by reference to FIG. 2. Parenthetically, in order to make clear difference in the parameter value between the fluoroscopy and the radiography, the parameters for the radiography are each affixed with prime.

The individual parameters are set manually or automatically on a parameter-by-parameter basis. However, of the parameters shown in FIG. 2, those concerning the camera mode, the I.I. mode, the x-ray irradiation field 13, setting of a concerned part of the object under inspection, the type of the X-ray filter 2, the type of the X-ray grid 6 and the air gap are set manually by the operator through the medium of the remote control/manipulation console 11 or the control/manipulation console 12. The type of the X-ray filter 2 may also be set automatically by selecting the type of the X-ray filter 2 in dependence on the tube voltage in the fluoroscopy mode as well as in the radiography mode. Furthermore, relation between the tube voltages and the type of the X-ray filters 2 as employed may be set by the inspector in precedence.

Of the parameters set manually, those for the camera mode, the I.I. mode and the X-ray irradiation field 13 are set to values which differ between setting 201 for the fluoroscopy and setting 202 for the radiography, while the other parameters are set to values which are common to the fluoroscopy mode and the radiography mode (fluoroscopy/radiography-common setting 203). On the other hand, of the parameter pairs shown in FIG. 2, the values of the tube voltage V, the tube current quantity Q, the optical iris aperture area $\Omega$ and the gain G, respectively, are automatically set not only in the fluoroscopy mode but also in the radiography mode, as described previously. More specifically, the parameters denoted collectively by 204 are set through the automatic control for the fluoroscopy while the parameters denoted collectively by 205 are set through the automatic control for the radiography. In this conjunction, it goes without saying that the tube voltage V for the radiography can be set manually by the inspector through the medium of the remote control/manipulation console 11 or the control/manipulation console 12.

Figure 3:
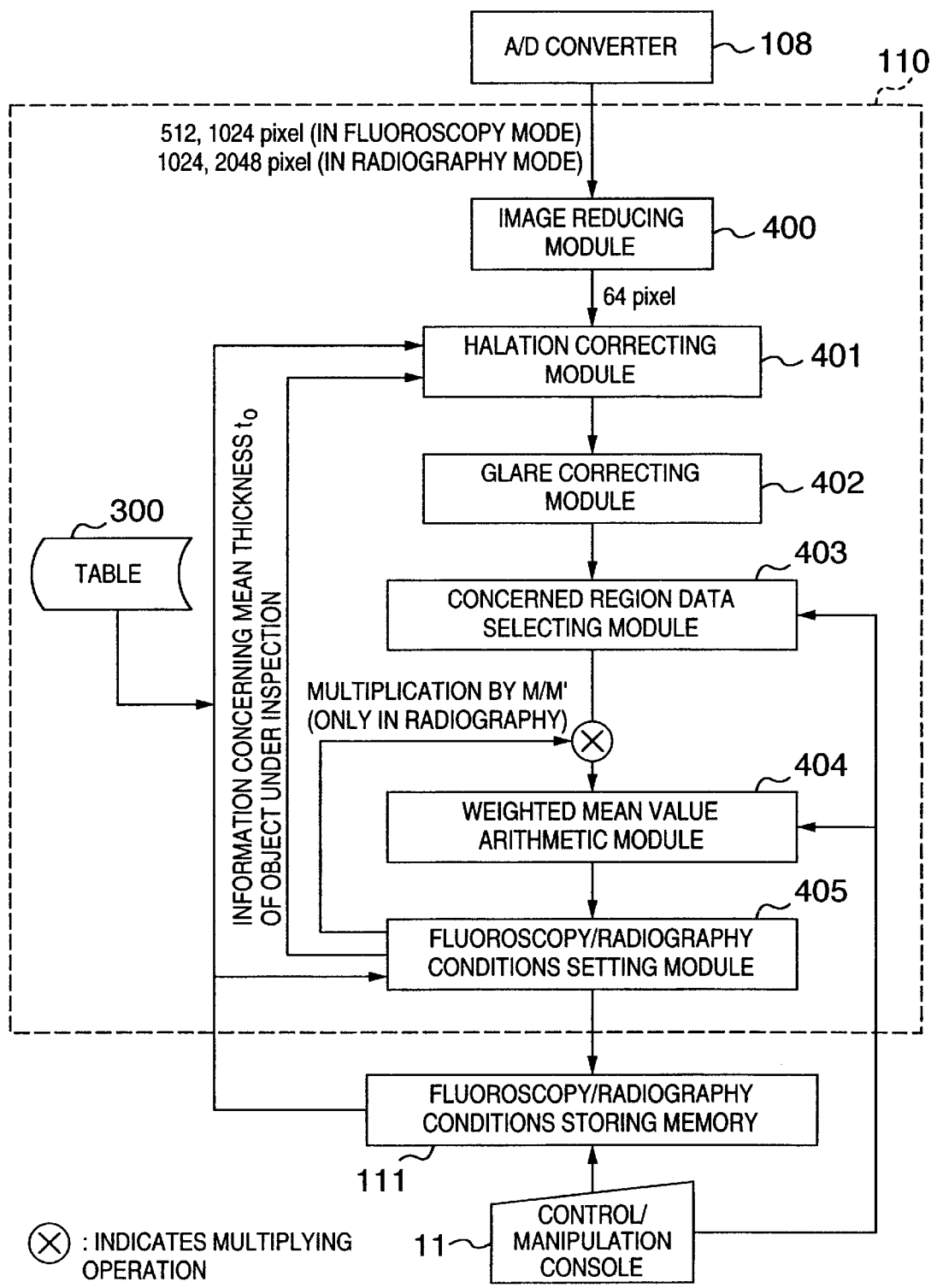
FIG. 3 is a flow chart for illustrating operations performed by a fluoroscopy/radiography conditions arithmetic unit according to the present invention.

FIG. 3 illustrates flows of operations performed by the fluoroscopy/radiography conditions arithmetic unit according to the instant embodiment of the invention. In the following, description will be directed to operations performed by the fluoroscopy/radiography conditions arithmetic unit.

A table 300 prepared in a memory stores the parameters used for correction of halation and setting of the conditions for fluoroscopy/radiography for rendering available the parameters.

An image reducing module 400 is designed to convert (reduce) the fluoroscopic image or the preliminary radiographic image resulting from conversion to the digital image by the A/D converter 108 to a digital image having a number of pixels (number of picture elements) set previously by the inspector through thinning or pixel addition processing. In the case of the instant embodiment of the invention, the digital image inputted from the A/D converter 108 is reduced or contracted to a digital image of a size of 64×64 pixels. In this conjunction, those of the reduced digital images which are used for determination of the conditions for the fluoroscopy/radiography among others will be referred to as "reference image". In this way, by using the reference image having a reduced number of pixels instead of the digital image resulting from the A/D conversion, overhead involved in the arithmetic operations performed subsequently (overhead involved in determination of the conditions for the fluoroscopy and the radiography) can be reduced, whereby succeeding arithmetic operations can be accomplished at higher speed. Parenthetically, the image size of the image inputted from the A/D converter 108 is determined in dependence on the camera mode as set. By way of example, the image size for the fluoroscopy is 512 or 1024 pixels while for the radiography, it is 1024 or 2048 pixels.

A halation correcting module 401 serves as an arithmetic means for computing or arithmetically determining the pixel values I of the individual pixels in a halation region in which the pixel value amount to 4095, by using the expression 1 on the basis of the thickness t determined for the extent or size of the halation region and the relevant X-rays conditions. The thickness t of the object under inspection is determined on the basis of a mean thickness $t_o$ of the object under inspection as calculated by a fluoroscopy/radiography conditions setting module 405 which will be described hereinafter. With the halation region, it is contemplated to mean a saturated region which makes appearance in the X-ray image when the output video signal before undergoing the A/D conversion is so large as to exceed the dynamic range of the video signal which can be quantized by the A/D converter 108. In the case of the instant embodiment, it is presumed that in the A/D converter 108, quantization is performed with a quantization bit number of 12 bits. Consequently, the pixel value within the halation region assumes 4095. However, the pixel value within the halation region can inherently assume a greater value than 4095, giving rise to error which presents a cause for degrading accuracy of the fluoroscopy and radiography controls. For this reason, the halation correcting module 401 is provided for computing the pixel value within the halation region with a view to compensating for the error. For more particulars, description will be made later on.

A glare correcting module 402 serves for performing glare correction on the reference image with the aid of a glare correction-destined digital filter set previously. With the glare correction, it is contemplated to mean a processing for eliminating scattered light ray components admixed into the X-ray image due to scattering of light rays taking place on the fluorescence screen of the X-ray I.I. 7. A concerned region data selecting module 403 is designed to set within the reference image undergone the glare correction a concerned location or region decided to be observed among others by the inspector not shown.

A weighted mean value arithmetic module 404 is designed to perform a weighting processing on the data selected in the concerned region to thereby ensure proper and correct values for the output image of a concerned part to be imaged which is of high importance for the diagnosis.

A fluoroscopy/radiography conditions setting module 405 is designed to determine the X-ray conditions so that a weighted image mean value M' can assume a predetermined value M within the dynamic range set by the inspector.

As the predetermined value M, a middle value of the dynamic range of the pixel values or a lower value than the former may be set.

In the fluoroscopy mode, feedback control of the tube voltage V is performed so that the weighted image mean value M' converges to the preset value M by executing the processing modules 400 to 405 upon every fetching of new fluoroscopic images.

On the other hand, in the radiography mode, the feedback control mentioned above can not be effectuated because the time for the radiography is very short. Accordingly, the X-rays conditions for setting the weighted mean value M equal to the preset value M are arithmetically determined in accordance with a method described hereinafter with the aid of a computer.

Figure 4A:
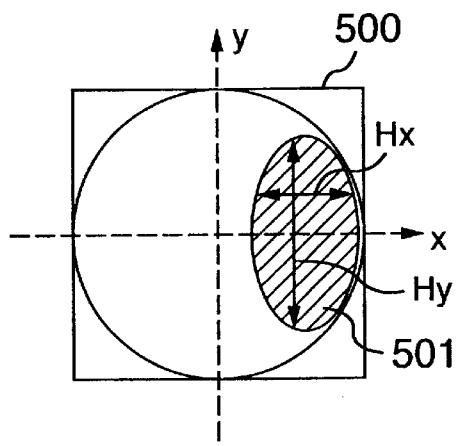
FIGS. 4A and 4B are views for illustrating operation of a halation correcting module according to the instant embodiment of the invention.
Figure 4B:
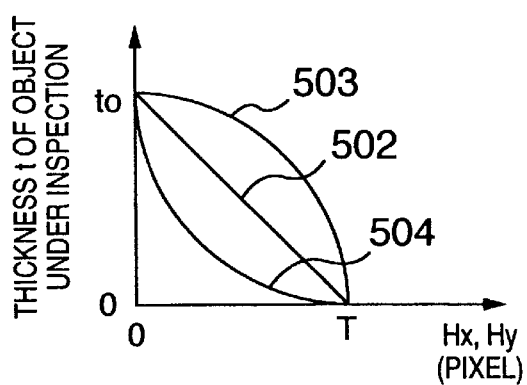

FIGS. 4A and 4B are views for illustrating a halation correcting operation in the X-ray apparatus according to the instant embodiment of the invention. More specifically, FIG. 4A is a view for illustrating a procedure of computing pixel values with the halation region, and FIG. 4B is a view for illustrating a procedure of determining the thickness t of the object under inspection on the basis of the extent or size of the halation region.

In the first place, description will be made of the procedure for calculating or computing the pixel values in a halation region making appearance in a reference image 500 by reference to FIG. 4A.

When the halation region 501 makes appearance in the reference image 500, the halation region 501 is detected as pixels whose pixel value assumes "4095", the maximum output value of the A/D converter.

Thus, the halation correcting module 401 is capable of arithmetically determining the pixel value within this halation region in accordance with a computing procedure described below.

At first, at individual positions in the x-direction on the reference image 500, extent or size Hy of the halation in the y-direction is measured. At that time, the thickness t of the object under inspection in the halation region is approximated at each of the x-positions in accordance with the extent or size Hy. Similarly, at individual positions in the y-direction on the reference. image 500, extent or size Hx of the halation in the x-direction is measured to thereby approximate the thickness t of the object under inspection in the halation region. Thus, there exist a couple of thicknesses t of the object under inspection which have been approximated for each of the pixels within the halation region 501. Accordingly, the thickness of the object under inspection at each of the pixels is determined as a mean value of the approximated values.

Next, description will turn to a method of determining the thickness t of the object under inspection on the basis of the extents or sizes Hx and Hy of the halation. Incidentally, in FIG. 4B, the size (number of the pixels or number of picture elements) of Hx or Hy is taken along the abscissa while the thickness t of the object under inspection taken is along the ordinate.

The thickness t of the object under inspection within the halation region is determined on the basis of the extents or sizes of Hx and Hy. Relation between the thickness t and the sizes of Hx and Hy can be approximated by a preset straight line 502 or simple curves 503, 504 or the like. However, when the sizes Hx and Hy are of such extent which exceeds a pixel number T, the thickness t of the object under inspection within the halation region is regarded as being "0" (zero). By contrast, in the case where Hx and Hy are small, the thickness t of the object under inspection approaches to a mean thickness $t_o$ of the object under inspection in the reduced image 500.

In this manner, the thickness t of the object under inspection is determined relatively to the mean thickness $t_o$ of the object under inspection in the reduced image 500. In the X-ray fluoroscopy mode, the mean thickness $t_o$ of the object under inspection can be determined inversely from the mean value I of the fluoroscopic image output and the conditions for the fluoroscopy in accordance with the expression 1. Similarly, when the halation correction is performed on the preliminary X-ray radiography, the mean thickness $t_o$ of the object under inspection acquired at the end of the fluoroscopy may be made use of. Parenthetically, the mean thickness $t_o$ of the object under inspection is arithmetically determined or computed by the fluoroscopy/radiography conditions setting module, information resulting from which is supplied to the halation correcting module 401. It is however to be noted that the mean thickness $t_o$ of the object under inspection is set to zero at the start of the fluoroscopy.

Finally, on the basis of the mean thicknesses $t_o$ of the object under inspection determined for the individual pixels and the relevant X-ray conditions, the individual pixel values I are computed in accordance with the expression 1 as the pixel values within the reduced image 500, whereupon the halation correction is completed.

Figure 5A:
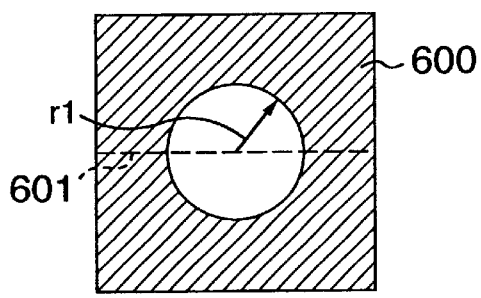
FIGS. 5A to 5D are views for illustrating a procedure of preparing a glare correcting filter for correcting glare scattering according to the instant embodiment of the invention.
Figure 5B:
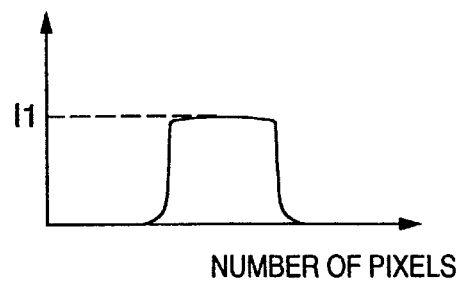
Figure 5C:
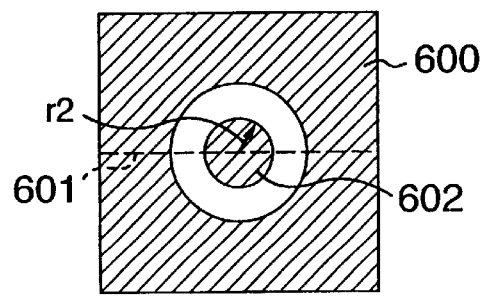
Figure 5D:
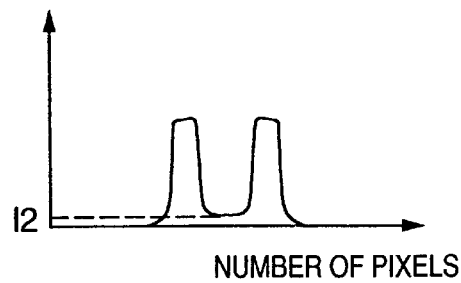

FIGS. 5A to 5D are views for illustrating a procedure of preparing or creating a glare correcting filter for correcting the glare scattering in the X-ray apparatus according to the instant embodiment of the invention. More specifically, FIGS. 5A and 5C are views for illustrating a front-side image of a phantom employed for measuring a point spread function of glare scattering, and FIGS. 5B and 5D are profile diagrams for illustrating relations between the pixel values of a picked-up image and distributed positions of the pixel values. Incidentally, the phantom illustrated in FIG. 5A may be constituted by, for example, a lead plate 600 having a through-hole formed at a center of the lead plate and having a radius r1, while the phantom shown in FIG. 5C is constituted by a disk-like lead plate 602 disposed at a center of the through-hole of the lead plate 600 and having a radius of r2.

As described hereinbefore, with the glare correction, it is contemplated to mean a processing for eliminating those light rays scattered mixedly into the X-ray image on the fluorescent output screen of the X-ray I.I. 7. In particular, when halation occurs in the image, a large quantity of light rays is admixed into the reference image due to the glare scattering taking place in the halation region, giving rise to a cause for lowering accuracy of the X-ray fluoroscopy control and the X-ray radiography control.

In general, the glare scattered point spread function h can be approximated by an exponent function, as represented by the expression 2 mentioned below.

$$h(x, y) = \left(1 + \frac{2\pi a}{b^2}\right)\delta(x)\delta(y) + ae^{-b\sqrt{x^2+y^2}} \quad \text{[Expression 2]}$$

Thus, frequency characteristic 1/H of the glare correcting filter for turning back the reference image to the image before being subjected to the glare scattering can be given by the following expression 3.

$$\frac{1}{H(\omega_x, \omega_y)} = \frac{1}{1 - \frac{2\pi a}{b^2} + \frac{2\pi ab}{(b^2 + \omega_x^2 + \omega_y^2)^{\frac{3}{2}}}} \quad \text{[Expression 3]}$$

In this manner, the glare correcting module 402 carries out the glare correction with the aid of a digital filter given by the expression 3. In the expression 2 and the expression 3, a and b represent parameters which characterize the point spread function. Accordingly, these parameters have to be measured in precedence.

Next, description will be made of a method of measuring the values of the parameters a and b of the glare scattered point spread function.

In the measurement of the glare scattered point spread function, it is presumed that the phantom is disposed along the straight lines of the X-ray grid and that neither the object 4 under inspection nor the bed top board 5 are disposed. On these conditions, the X-ray radiography is carried out for the phantoms shown in FIGS. 5A and 5C, respectively. In that case, profiles representing the pixel values of the picked-up images and the distributed positions of the pixel values are such as illustrated in FIGS. 5B and 5D, respectively, where the profile is that on a straight line 601 which extends through the center of the lead plate 600.

Referring to FIGS. 5B and 5D, representing the pixel values at the center positions of the through-holes formed in the lead plates 600 by I1 and I2, respectively, the parameter a of the point spread function can be given by the following expression 4 by using the pixel values I1 and I2 and the parameter b.

$$a = \frac{b^2}{2\pi} \frac{I_1/I_2}{(1+br_2)e^{-br2} + (I_1/I_2 - 1)(1+br_1)e^{-br1}} \quad \text{[Expression 4]}$$

Thus, by placing the parameter given by the expression 4 in the expression 3, the parameters appearing in the expression 3 can be limited to only the parameter b. Thus, by performing the glare correction on the picked-up image of the phantom shown in FIG. 5C with b as variable, it is possible to determine the value of b such that the value of I2 in the image profile after the glare correction is "0" (zero). Further, the value of a can equally be determined on the basis of the determined value of b in accordance with the expression 4. Thus, the frequency characteristic of the glare correcting filter can be determined.

Figure 6:
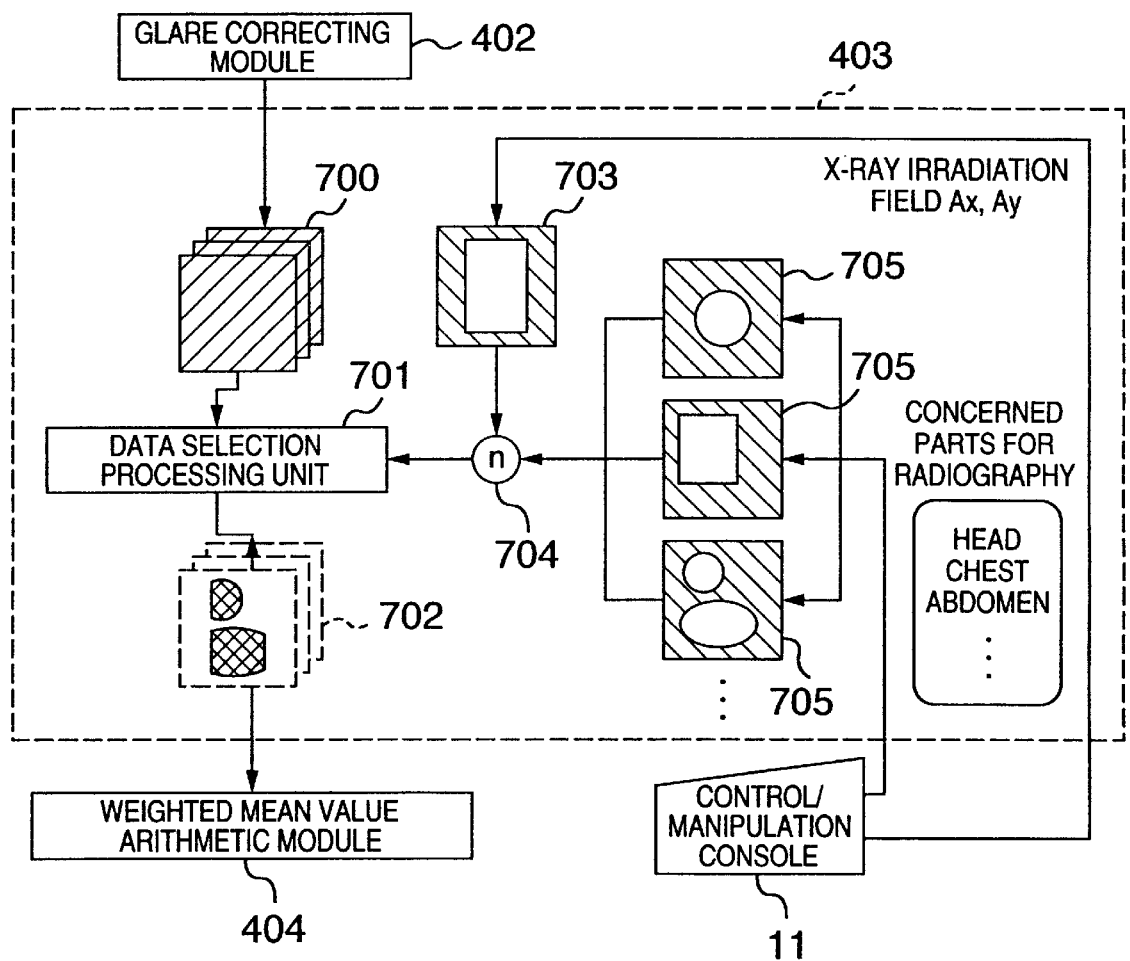
FIG. 6 is a view for illustrating operation of a concerned region data selecting module according to the instant embodiment of the invention.

FIG. 6 is a view for illustrating operation of the concerned region data selecting module 403 in the X-ray apparatus according to the instant embodiment of the invention.

In general, the concerned region for the radiography will differ from one to another in dependence on the concerned part destined for radiography of the object 4 under inspection. Accordingly, the inspector sets previously the radiography-destined concerned part of the object 4 under inspection through the medium of the remote control/manipulation console 11. In that case, a concerned region mask 705 employed for selecting only the data within the concerned region is prepared previously for each of the radiography-destined concerned parts and selected in conformance with the preset value of the radiography-destined concerned part. Incidentally, it should be mentioned that in the X-ray fluoroscopy, the concerned region set with the concerned region mask 705 can also be varied arbitrarily with a means which will be described hereinafter.

Subsequently, the concerned region mask 705 as selected is logically ANDed with a mask 703 for the X-ray irradiation used for selecting only the data within the X-ray irradiation field by means of a logical product or AND arithmetic module 704. Consequently, with the mask (selected mask) outputted from the logical product arithmetic module 704, only the region lying within both the concerned region and the X-ray irradiation field is selected. Incidentally, the X-ray irradiation field mask 703 is prepared in dependence on the X-ray irradiation field in the fluoroscopy mode as well as in the radiography mode as set through the medium of the remote control/manipulation console 11.

Finally, data select processing is performed on the reference image 700 by the data selection processing module 701 for selecting only the data within the region determined by the logical product arithmetic module 704, whereby only the selected data 702 is outputted from the concerned region data selecting module 403. Parenthetically, it should be mentioned that the data selection processing module 701 and the logical product arithmetic module 704 mentioned above may be realized, respectively, by program or hardware.

Figure 7A:
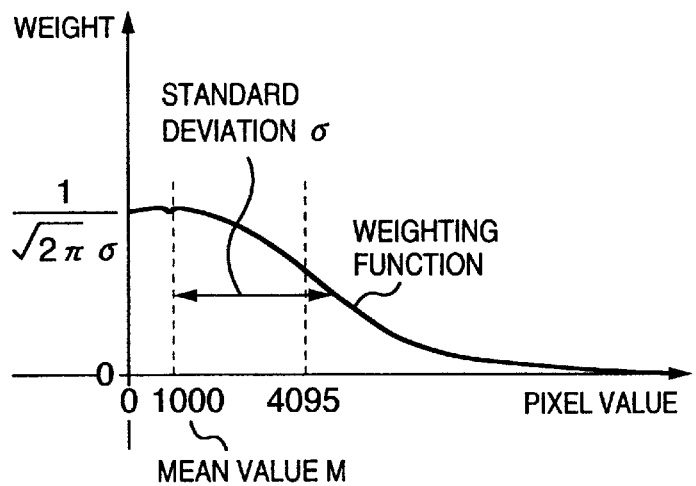
FIGS. 7A and 7B are views for illustrating the principle of a weighted mean value arithmetic unit according to the instant embodiment of the invention.
Figure 7B:
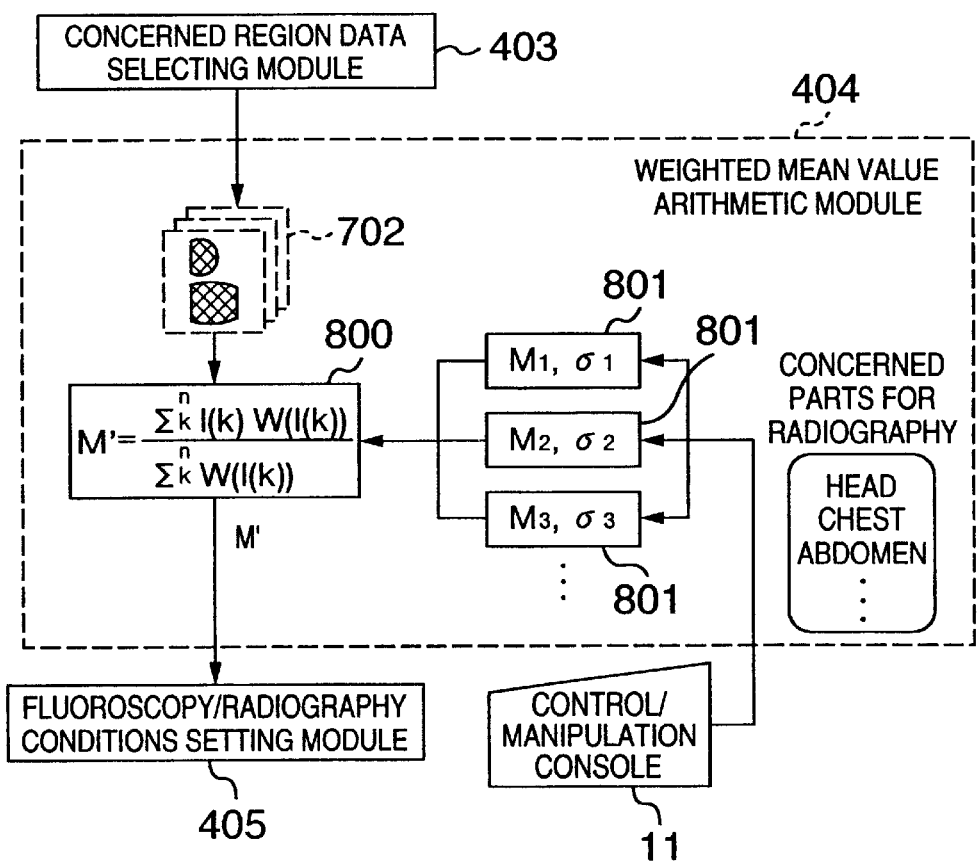

FIGS. 7A and 7B show views for illustrating arithmetic operation of the weighted mean value arithmetic module 404 in the X-ray apparatus according to the instant embodiment of the invention. In the following, description will be made in detail of the weighted mean value arithmetic determination processing by reference to FIGS. 7A and 7B, in which FIG. 7A is a view for illustrating a weighting function employed in the X-ray apparatus according to the instant embodiment of the invention, and FIG. 7B is a diagram for illustrating a processing procedure executed by the weighted mean value arithmetic module 404.

For the data selected by the concerned region data selecting module 403, the weighting function illustrated in FIG. 7A is first multiplied in dependence on the individual pixel values, which is then followed by computation of a mean value for all the data derived after the multiplication of the weighting function. As can be seen in FIG. 7A, the weighting function can be represented by a normal distribution as a function of a variable, i.e., the pixel values or values of picture elements of the data. The normal distribution mentioned above can be definitely determined by the mean value M and the standard deviation σ as set. For this reason, such arrangement is adopted that values of the mean value M and the standard deviation σ can be set by the inspector as parameters for expressing the weighting function. Furthermore, in the X-ray apparatus according to the instant embodiment of the invention, by multiplying the weighting function for a histogram of the data 702 selected by the concerned region data selecting module 403, it is possible to mitigate effectively the influence exerted to the exposure control in the X-ray fluoroscopy by the image information of concerned part(s) of less significance for the diagnostics such as the image information of the concerned part(s) of the selected data in which the pixel value is extremely high and/or extremely low.

A histogram represents a distribution of numbers of data corresponding to image intensities (pixel values) of an X-ray image. As the x-ray image providing a basis for generation of the histogram, there may be employed, for example, a fluoroscopic image or an image picked up preliminarily with feeble X-ray conditions than those in the intrinsic radiography.

Now, representing the weighted mean value by M', the pixel number of the data 702 selected by the concerned region data selecting module 403 by n and the pixel values of the individual picture elements by I(k) (k=1~n), then M' can be arithmetically determined in accordance with the undermentioned expression 5.

$$M' = \frac{\sum_{k=1}^{n} I(k)W(I(k))}{\sum_{k=1}^{n} W(I(k))} \quad \text{[Expression 5]}$$

where W represents a weighting function.

Next, referring to FIG. 7B, description will be directed to the processing procedure executed by the weighted mean value arithmetic module 404.

As described hereinbefore, since the parameters M and σ of the weighting function have pertinent values which differ from one to another concerned part destined for the radiography, there are previously set proper values ($M_1$, $σ_1$; $M_2$, $σ_2$; . . . ; $M_n$, $σ_n$) for every concerned part destined for the radiography. When the inspector sets a radiography-destined concerned part of the object 4 under inspection through the medium of the remote control/manipulation console 11, proper values 801 of M and σ are selected on the basis of the preset values mentioned above. Incidentally, in the X-ray fluoroscopy, the values of M and σ can be varied arbitrarily with the aid of a means which will be described later on. By using the values 801 of M and σ as selected, a weighting function is determined, whereon a weighted mean arithmetic determination 800 represented by the expression 5 is performed on the selected values 801 of M and σ, whereby the weighted mean value M' is computed.

In the X-ray apparatus according to the instant embodiment, because the weighting function of normal distribution is employed, the inspector can manipulate intuitively the weighting function, to an advantageous effect. However, the weighting function is never restricted to that of normal distribution. There may be employed probability distribution functions such as, for example, $\chi^2$ (chi-square)-distribution having a degree of freedom not smaller than "3", Poisson distribution, t-distribution or the like.

Figure 8A:
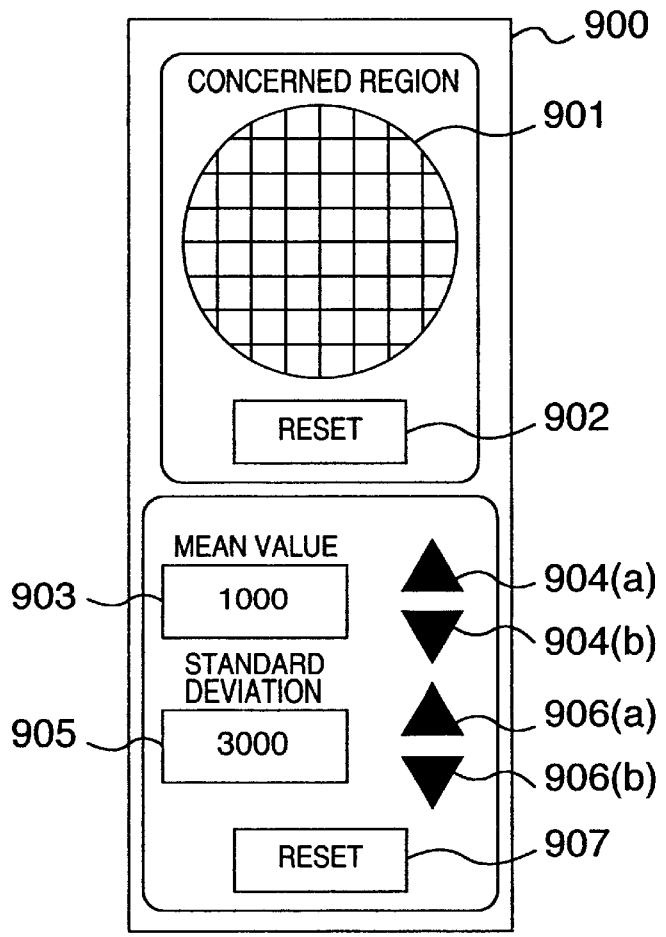
FIGS. 8A to 8C are views for illustrating operations of a parameter setting means for changing arbitrarily a concerned region mask and values of parameters M and $\sigma$ of a weighting function in an X-ray fluoroscopy mode.
Figure 8B:
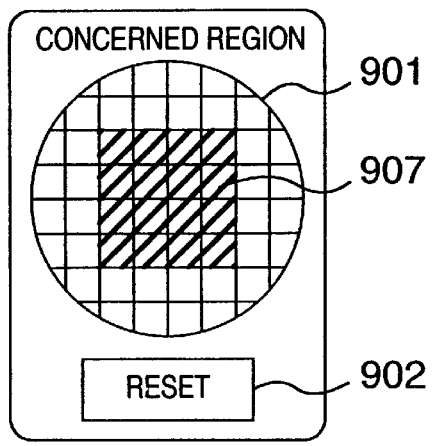
Figure 8C:
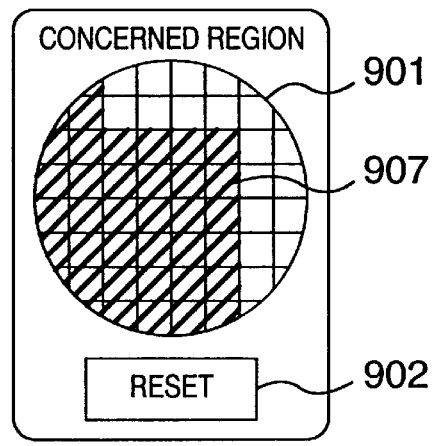

FIGS. 8A to 8C are views for illustrating operations of a parameter setting means for changing arbitrarily the concerned region mask and the values of parameters M and σ of the weighting function in the X-ray fluoroscopy mode. In the following, operations of the parameter setting means will be described by reference to FIGS. 8A to 8C, in which FIG. 8A is a view showing an outer appearance of the parameter setting means, FIG. 8B is a view for illustrating a procedure of setting a concerned region, and FIG. 8C is a view for illustrating a state succeeding to the setting or establishment of a concerned region.

In general, since the concerned region and the parameter values of the weighting function have proper values which differ in dependence on individual difference of the object 4 under inspection, a proper X-ray fluoroscopy control can be realized by effectuating modifications in the X-ray fluoroscopy mode. In the X-ray fluoroscopy control according to the instant embodiment, setting of the concerned region and the parameters M and σ is carried out by resorting to a controller 900 which is susceptible for remote manipulation and which can be disposed on the control/manipulation console 12 and the remote control/manipulation console 11 as well.

As shown in FIG. 8A, setting of the concerned region can be realized by using a concerned region setting button 901 and a reset button 902. The concerned region setting button 901 is constituted by a large number of buttons disposed in an array having an outer frame of a circular form which corresponds to a region or field adapted to be detected by the X-ray I.I. The individual buttons of the button array can be turned on and off independently from one another. By pushing the buttons, on- and off-states are realized sequentially and repetitionally. Further, the button array is implemented in such structure that only in the on-state of the button, the button itself emanates light or alternatively color of the button is changed. To this end, the concerned region setting button 901 may be implemented by using touch sensors which per se are well known in the art.

Next, description will turn to the concerned region setting procedure by reference to FIG. 8B. When the inspector sets a concerned part destined for the radiography through the medium of the remote control/manipulation console 11, only buttons 907 that correspond to the concerned region set for the radiography-destined concerned part are automatically set to the on-state while emitting light (the buttons indicated by hatching in FIG. 8B). Subsequently, when the inspector desires to change the concerned region in the X-ray fluoroscopy mode, the inspector pushes or touches the relevant buttons of the concerned region setting button 901 to thereby set arbitrarily the relevant buttons of the concerned region setting button 901 to the on- or off-state, whereby the concerned region desired by the inspector can be set or established, as illustrated in FIG. 8C. However, in order to prevent the concerned region from being set outside of the X-ray irradiation field, the button corresponding to the extra-X-ray-irradiation-field is constantly held fixedly in the off-state. In this conjunction, it is noted that when the concerned region as set is excessively small, the X-ray fluoroscopy control will become unstable. Accordingly, a minimum area is previously set for the concerned region, and when the area of the concerned region as set becomes smaller than the minimum area, the on-state of the concerned region setting button 901 is held fixedly as it is.

As described hereinbefore, when the concerned region is changed, the outer frame of the concerned region as set or established is displayed on the monitor 10 for a predetermined time. Parenthetically, the concerned region set newly in this manner can be reset to the initial state illustrated in FIG. 8B by pushing the reset button 902. Further, the concerned region determined through the procedure described above can again be set newly or altered for the radiography-destined concerned part.

Next, in the procedure for setting the parameters M and σ of the weighting function, these parameters are set by using mean value setting buttons (functional parameter setting means) 904($a$) and ($b$) and standard deviation setting buttons (functional parameter setting means) 906($a$) and ($b$), respectively. The values of the parameters M and σ as set are always displayed on a mean value display window 903 and a standard deviation display window 905. At first, a concerned part destined for radiography is set through the medium of the remote control/manipulation console 11. Then, values of the parameters M and σ are initially set for the radiography-destined concerned part to be subsequently displayed within the mean value display window or frame 903 and the standard deviation display window or frame 905, respectively. When the parameter M is to be changed in the X-ray fluoroscopy mode, the mean value setting button 904($a$) or ($b$) is pushed to thereby increase or decrease the value of the parameter M. In this conjunction, it is noted that the value of the parameter M can be changed only within a preset range set previously. Similarly, when the parameter σ is to be changed in the X-ray fluoroscopy mode, the standard deviation setting button 906($a$) or ($b$) is pushed to thereby increase or decrease the value of the parameter σ. The value of the parameter σ can be changed only within a range set previously. Further, the values of the parameters M and σ set newly through the procedure described above can be set back or reset to the initial state by pushing the reset button 907. Besides, the values of M and σ determined through the procedure described above can again be set newly or altered for the radiography-destined concerned part.

Figure 9A:
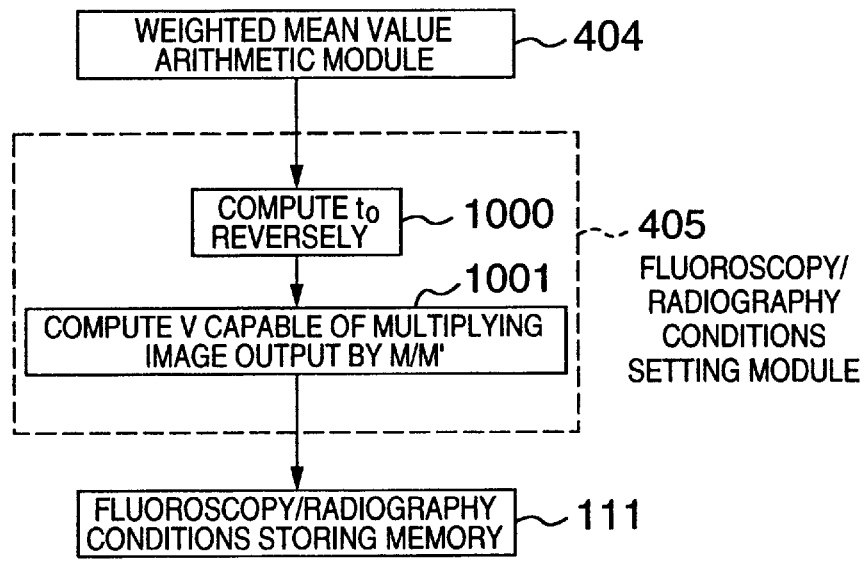
FIGS. 9A and 9B are views for illustrating operations of a fluoroscopy/radiography conditions setting module according to the instant embodiment of the invention.
Figure 9B:
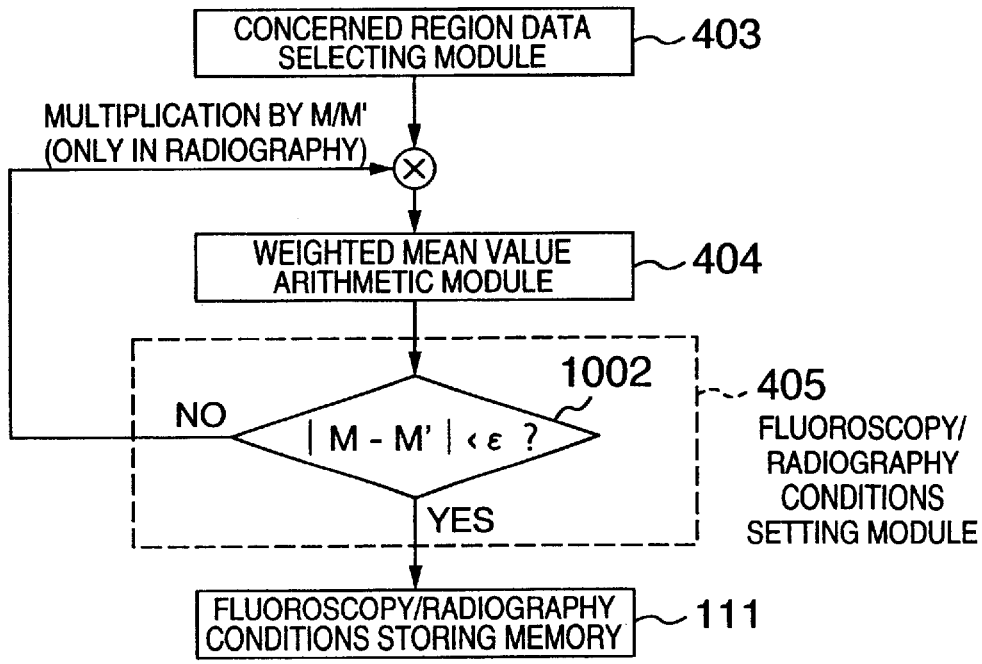

FIGS. 9A and 9B are views for illustrating operation of the fluoroscopy/radiography conditions setting module 405 in the X-ray apparatus according to the instant embodiment. More specifically, FIG. 9A is a view for illustrating operation of the fluoroscopy/radiography conditions setting module in the X-ray fluoroscopy mode, and FIG. 9B is a view for illustrating operation of the fluoroscopy/radiography conditions setting module in the X-ray radiography mode.

At first, with reference to FIG. 9A, description will be directed to the fluoroscopy conditions setting procedure in the X-rays fluoroscopy mode.

In the X-ray fluoroscopy mode, it is necessary to determine the values of the tube voltage V and the tube current quantity Q of the X-ray tube 1, the optical iris aperture area Ω and the gain G of the amplifier 107, respectively. However, the value of the tube current quantity Q for the fluoroscopy can be ordinarily determined on the basis of the tube voltage V for the fluoroscopy, and thus the tube current quantity for the fluoroscopy can be expressed as a function Q(V) of the tube voltage V. Further, the optical iris aperture area Ω is maintained to be constant in the fluoroscopy mode. Additionally, the gain G of the amplifier 107 is determined in dependence on the camera mode. Accordingly, it is sufficient to take into consideration only the tube voltage V for the fluoroscopy as the parameter to be controlled in the fluoroscopy mode. In other words, setting of the tube voltage V for the fluoroscopy which makes available the image output multiplied by M/M' is required only for allowing the weighted mean value M' to converge to M. To this end, the tube voltage V for the fluoroscopy which allows multiplication of the image output I by M/M' is determined in accordance with the expression 1, whereby the fluoroscopic image can be controlled appropriately.

Next, description will be directed to a procedure for arithmetically determining the tube voltage V for the fluoroscopy. At first, the mean thickness $t_o$ of the object under inspection is computed reversely by placing M' in the image output I at the left term of the expression 1 (step 1000). In this conjunction, reversal computation of the mean thickness $t_o$ of the object under inspection can be realized by resorting to a numerical value computation means such as a division-by-two method or the like.

Subsequently, the fluoroscopy/radiography conditions setting module 405 changes the tube voltage V for the fluoroscopy on the basis of the mean thickness $t_o$ of the object under inspection, the tube voltage V for the fluoroscopy and the tube current quantity Q(V) for the fluoroscopy in accordance with the expression 1, to thereby determine the tube voltage V such that the image output I appearing at the left term of the expression 1 becomes equal or converges to M (step 1001). In this conjunction, data concerning the mean thickness $t_o$ of the object under inspection can equally be made use of in the processing performed by the halation correcting module 401.

The tube voltage V for the fluoroscopy as well as the tube current quantity Q(V) for the fluoroscopy as determined in the steps 1000 and 1001 are recorded on (stored in) the fluoroscopy/radiography conditions storing memory 111 to be immediately reflected in the output power of the X-ray tube 1. Through the procedure described previously, the feedback control in the X-ray fluoroscopy mode can be carried out. In general, the weighted mean value M' determined arithmetically for a reference image as obtained newly through the procedure described previously can not straightforwardly represent the preset value M, which is ascribable to the weighting arithmetic operation by its very nature. However, in the X-ray fluoroscopy mode according to the instant embodiment of the invention, the weighted mean value M' can converge to the value M by carrying out the feedback control only a few or several times.

Next, referring to FIG. 9B, description will turn to a procedure for setting the radiography conditions in the X-ray radiography mode.

In the X-ray radiography mode, it is required to compute the values of the tube current quantity Q' of the. X-ray tube 1, the optical iris aperture area Ω' and the gain G', respectively. However, in the radiography mode, the optical iris aperture area Ω' is ordinarily held at a constant value. Additionally, the gain G' of the amplifier 107 is determined in dependence on the camera mode. Accordingly, it is sufficient to take into consideration only the tube current quantity Q' for the radiography as the parameter to be controlled in the radiography mode. In other words, setting of the tube current quantity Q' for the radiography which makes available the image output I multiplied by M/M' is only required for causing the weighted mean value M' in the preliminary radiography mode to converge to the preset value M. However, even when the intrinsic X-ray radiography is performed with the tube current quantity Q' for the radiography as set in this manner, the weighted mean value of the picked-up X-ray image can not straightforwardly represent the preset value M, which is ascribable to the weighting arithmetic by its nature, as in the case of the X-ray fluoroscopy described previously. Furthermore, in the intrinsic X-ray radiography, it is impossible to make the value M' approach the value M through the feedback control, differing from the case of the X-ray fluoroscopy mode. Accordingly, in order to determine arithmetically the tube current quantity Q' accurately for the radiography, processings described below are executed.

At first, in the preliminary X-ray radiography mode, data outputted from the concerned region data selecting module 403 is once stored in a memory not shown. Subsequently, on the basis of the data saved in the above-mentioned memory, the weighted mean value M' is computed by the weighted mean value arithmetic module 404. In succession, the absolute value of difference between M and M' is arithmetically determined by the fluoroscopy/radiography conditions setting module 405, whereon it is decided whether or not the difference mentioned above is smaller than ε (step 1002). When it is decided in the step 1102 that the absolute value of the difference between M and M' is smaller than ε, the tube current quantity Q' for the radiography is regarded as being set to a proper value, and the weighted mean value M' at that time is recorded on (stored in) the fluoroscopy/radiography conditions storing memory 111. On the other hand, when the absolute value of the difference between M and M' is greater than ε, the tube current quantity Q' for the radiography is regarded as not being set to the proper value, and thus the fluoroscopy/radiography conditions setting module 405 determines newly a proper value of the tube current quantity Q' for the radiography by multiplying the tube current quantity Q' for the radiography by M/M', the result of which is then outputted to the weighted mean value arithmetic module 404. Further, the fluoroscopy/radiography conditions setting module 405 is designed to multiply all the data stored in the memory not shown (data inputted from the concerned region data selecting module 403) by M/M', whereon data resulted from the multiplication are overwritten in the memory not shown for updating the data stored in that memory.

On the other hand, upon updating of the data by the fluoroscopy/radiography conditions setting module 405, the weighted mean value arithmetic module 404 again performs arithmetic determination of the weighted mean value M' on the basis of the updated data to output the weighted mean value as determined to the fluoroscopy/radiography conditions setting module 405, which responds thereto by arithmetically determining the absolute value of difference between M and M', whereon decision is made as to whether or not the difference is smaller than ε (step 1002).

The fluoroscopy/radiography conditions setting module 405 performs repetitively the procedure described above until the absolute value of difference between M and M' becomes smaller than ε, whereby the weighted mean value M' is made to approach progressively the value M to thereby determine arithmetically the proper tube current quantity Q' for the radiography, i.e., proper or optimal conditions for the radiography.

In this way, the fluoroscopy/radiography conditions setting module 405 of the X-ray apparatus according to the instant embodiment is capable of setting the optimal or proper tube current quantity for the radiography in precedence to the intrinsic radiography, and thus the X-ray irradiation time can be controlled independently of the frame read time of the television camera 9.

Incidentally, the predetermined value ε may be stored in a table as the preset value or alternatively the inspector may set as a desired value through the medium of the control/ manipulation console 12 or the remote control/manipulation console 11 in precedence to the fluoroscopy/radiography. Further, the predetermined value $\epsilon$ is used a a coefficient which determines the accuracy or precision of the radiographically picked-up image. More specifically, as the predetermined value $\epsilon$ becomes smaller, the image precision is enhanced. On the other hand, when the time taken for arithmetic operation increases and the predetermined value $\epsilon$ is large, the image precision or accuracy becomes lowered. However, the time taken for the arithmetic can be decreased. Thus, the optimal value of the predetermined value $\epsilon$ lies within a range of $5 \leq \epsilon \leq 25$. By way of example, value "10", "15", etc. will be pertinent.

Furthermore, because the fluoroscopy/radiography conditions setting module 405 of the X-ray apparatus according to the instant embodiment is so designed that the tube voltage and the X-ray irradiation field can remain invariable in both the preliminary radiography mode and the intrinsic radiography mode, contrast of the image as well as ratio of the scattered X-ray quantity can be made to remain invariable between the preliminary radiography and the intrinsic radiography. Thus, the exposure dose for the radiography can be determined easily and simply. Besides, because the exposure dose in the radiography mode can be computed with high accuracy, the quality of the picked-up X-ray image can be enhanced.

On the other hand, the fluoroscopy/radiography conditions setting module 405 of the X-ray apparatus according to the instant embodiment of the invention may be so designed as to set the tube current quantity Q' for the intrinsic radiography mode to be smaller than the tube current quantity Q' for the radiography in the preliminary radiography mode. In that case, halation contained in the reference image can be suppressed to such extent as to allow the radiography control to be performed with high accuracy on the basis of the reference image, which in turn means that the quality of the picked-up X-ray image can be enhanced.

FIG. 10 shows a view for illustrating a data structure of the table employed in the X-ray apparatus according to the instant embodiment of the invention.

As can be seen from FIG. 10, the table 300 is composed of values 301 for every television mode $F_C$, values 302 for every I.I. mode and values 303 for every characteristics. However, because the characteristic values differ in dependence on all possible combinations of types of the grid and filter, tables may be prepared for all useable combinations of the grid and the filter. By way of example, this table may be prepared for each of the grid and filter combinations.

As is apparent from the foregoing description, in the X-ray fluoroscopy/radiography apparatus according to the instant embodiment of the invention, the weighted mean value arithmetic module 404 is so arranged that for the digital image representing the X-ray image picked up in the X-ray fluoroscopy mode or the preliminary radiography mode, the weighted mean value M' of the selected data is arithmetically determined in accordance with the expression 2 on the basis of the normal distribution in which variables introduced in terms of the weighting function represent the pixel values and the histogram of the pixel values of the selected data inputted from the concerned region data selecting module 403, while the fluoroscopy/radiography conditions setting module 405 is designed to arithmetically determine the tube voltage V for the fluoroscopy or the tube current quantity Q' for the radiography at which the weighted mean value M' becomes equal or converges closely to the mean value M of the weighting function, the result of which is stored in the fluoroscopy/radiography conditions storing memory 111, wherein the X-ray controller 100 regulates or adjusts the output power of the X-ray tube 1 on the basis of the stored value. Thus, the influence of the image information exerted by the concerned part having diagnostically lesser importance to the exposure control in the X-ray fluoroscopy mode can be minimized. In this manner, optimal image density can be ensured for the important concerned part of the object under inspection. Besides, because the conditions for fluoroscopy and radiography can be so controlled that image density of the diagnostically important concerned part can be optimized, quality of the X-ray fluoroscopic/radiographic image can be improved, as a result of which reliability of the diagnosis performed by the inspector can be enhanced. Besides, efficiency of the diagnosis performed by the inspector can also be enhanced. Additionally, in the X-ray apparatus according to the instant embodiment of the invention, because the normal distribution which is one of the forms of the probability distribution function is adopted as the weighting function, the inspector can recognize intuitively the profile of the function in the case where the parameters for the function are to be changed or the like.

Furthermore, since the weighted mean value M' can be obtained as the integrated value of the histogram inputted from the concerned region data selecting module 403 and the weighting function, i.e., since the weighted mean value M' has undergone the weighting processing, as can be understood from the expression 2, the X-ray apparatus according to the instant embodiment of the invention can carry out the fluoroscopy/radiography control such that the image output for the diagnostically highly important concerned part can assume optimal value.

Moreover, in the X-ray fluoroscopy/radiography apparatus according to the instant embodiment of the invention, the glare correcting module 402 performs the fluoroscopy/radiography control on the basis of the reference image from which the influence of the glare scattering has been eliminated, differing from the hitherto known X-ray apparatus, and thus the X-ray fluoroscopy conditions and the X-ray radiography conditions can be controlled so that optimal X-ray dose can always be ensured.

By way of example, there arises such situation that when halation makes appearance in an fluoroscopic image such as that of a lateral portion of Magen or stomach, a large proportion of the glare scattering occurring in the halation area will be admixed into the fluoroscopic image and may assume as much as 40% or so of the output signal. Consequently, in the case of the conventional X-ray fluoroscopy/radiography apparatus in which the X-ray fluoroscopy control is performed such that the output signal as a whole assumes a constant value or level, convergence of the control occurs in the state where the X-ray dose on the order of 60% of the optimal X-ray dose is outputted, which incurs degradation of the image quality, giving rise to a problem. By contrast, in the X-ray fluoroscopy/radiography apparatus according to the instant embodiment of the invention, the glare correcting module 402 is designed to carry out the X-ray fluoroscopy control on the basis of the reference image from which the glare components have been eliminated, and thus the control which allows the X-ray dose to assume approximately the optimal value or level can be realized. Thus, with the X-ray fluoroscopy/radiography apparatus according to the instant embodiment of the invention, improvement of ca. 40% or so in terms of the X-ray dose can be accomplished when compared with the conventional apparatus.

Besides, in the x-ray apparatus according to the instant embodiment of the invention, the pixel values in the halation region of the reference image are converted into proper pixel values by means of the halation correcting module 401 in precedence to performing the glare correction. Thus, the fluoroscopy and radiography control can be realized for practical applications even when the television camera 9 of a narrow dynamic range is employed for picking up the image.

Additionally, in the X-ray apparatus according to the instant embodiment of the invention, the aimed control can be carried out on the basis of the X-ray image picked up by the television camera 9. Thus, the structure of the X-ray apparatus can be simplified, whereby the X-ray diagnosis system of low cost can be provided.

Further, owing to the arrangement that control is performed on the basis of the X-ray image picked up by the television camera 9, sensitive reaction or response behavior of the sensor which may be brought about upon movement of the object under inspection can be suppressed effectively, which means that the fluoroscopic image can be picked up with stability.

Incidentally, in the X-ray fluoroscopy/radiography apparatus according to the instant embodiment of the invention, the image reducing module 400, the halation correcting module 401, the glare correcting module 402, the concerned region data selecting module 403, the weighted mean value arithmetic module 404 and the fluoroscopy/radiography conditions setting module 405 are implemented as programs. However, the invention is never restricted to such arrangement. Corresponding hardware units may be employed.

In addition, according to the invention incarnated in the illustrated embodiment, decision as to whether the tube current quantity Q' in the radiography mode is to be adopted or not is made on the basis of the decision as to whether the absolute value of difference between the mean value M as set and the weighted mean value M' is smaller than the predetermined value $\epsilon$ inclusive thereof. However, the invention is never restricted to such arrangement. It goes without saying that approximation with the ratio of M to M' (M/M') may be adopted.

It is not intended to limit the invention to the illustrated embodiment, but numerous modifications and combinations will readily be resorted to without departing from the gist and the scope of the present invention. Accordingly, all suitable modifications and equivalents may be resorted to, falling within the spirit and scope of the invention.

By way of example, although it has been described that the preliminary radiography is performed in precedence to the X-ray radiography, the optimal X-ray radiography conditions can equally be derived from the information concerning the mean thickness of the object under inspection determined arithmetically in the course of the X-ray fluoroscopy. As a method of determining the proper X-ray radiography conditions on the basis of the information concerning the mean thickness of the object under inspection, there can be mentioned, for example, the method described in Japanese Patent Application No. 8-267518. Furthermore, although the system comprised of the X-ray I.I. 7, the optical lens system 8 and the television camera 9 are employed as the X-ray detector in the illustrated embodiment, it goes without saying that comparable advantageous effects can be obtained even when a two-dimensional X-ray flat-panel sensor or the like is employed. A typical example of such two-dimensional X-ray flat-panel sensor can be found, for example, in "Large Area, Flat-Panel, Amorphous Silicon Imagers; L. E. Antonuk, et al. SPIE, Vol. 2432, Physics of Medical Imaging, pp. 216–227".

It should further be mentioned that the present invention can find application to conventional X-ray fluoroscopy apparatuses, X-ray radiography apparatuses, X-ray stereo-radiographic apparatuses, etc. as well.

What is claimed is:

1. An X-ray control method in an X-ray apparatus including an X-ray tube for generating X-rays to irradiate an object under inspection, X-ray irradiation field limiting means for limiting an X-ray irradiation field and imaging means for picking up an X-ray image of said object under inspection, comprising:

a step of arithmetically determining a mean value M' of a weighted histogram obtained by multiplying a histogram representing a distribution of numbers of data corresponding to image intensities in a reference image which is an X-ray image obtained from an output signal of said imaging means and a weighting function having a variable dependent on said image intensities; and a step of controlling output power of said X-ray tube so that said mean value M' approaches a mean value M of said weighting function.

2. An X-ray control method according to claim 1, wherein said step of arithmetically determining said mean value M' includes:

a step of selecting said reference image from a fluoroscopic image.

3. An X-ray control method according to claim 1, wherein said step of arithmetically determining said mean value M' includes:

a step of selecting said reference image from an X-ray image picked up previously through a preliminary X-ray radiography performed in precedence to an X-ray radiography on X-ray conditions which are weaker than X-ray conditions for the X-ray radiography.

4. An X-ray control method according to claim 3, wherein said step of controlling the output power of said X-ray tube includes:

a step of performing control so that a tube voltage of said X-ray tube and said X-ray irradiation fields remain same in both the preliminary X-ray radiography and the X-ray radiography.

5. An X-ray control method according to claim 1, wherein said step of arithmetically determining said mean value M' includes:

a step of selecting a probability distribution function as said weighting function: and a step of setting a mean value of said probability distribution function and a standard deviation of said probability distribution function, as functional parameters of said weighting function.

6. An X-ray control method according to claim 5, wherein said step of selecting said probability distribution function includes selecting a normal distribution function or an $\chi^2$-distribution having a degree freedom not smaller than three or a t-distribution, as said probability distribution function.

7. An X-ray control method according to claim 1, wherein said step of arithmetically determining said mean value M' includes:

a step of decreasing a number of pixels of said reference image relative to a number of pixels of an X-ray image in an X-ray fluoroscopy or in a preliminary X-ray radiography; and a step of arithmetically determining said mean value M' on the basis of a reference image having the decreased number of pixels.

8. An X-ray control method according to claim 1, wherein said step of arithmetically determining said mean value M' includes:
- a step of detecting a region in which halation occurs in said reference image;
- a step of performing computation of intensities of individual pixels within said region, on the basis of a control value for said X-ray tube, thickness of said object under inspection and a control value for said imaging means in the state where the halation is taking place;
- a step of performing replacement of the intensities of the pixels within said region by the intensities of the pixels determined by said computation; and
- a step of arithmetically determining said mean value M' on the basis of a reference image resulting from said replacement.

9. An X-ray control method according to claim 8, wherein said thickness of said object under inspection corresponding to said region is determined on the basis of extent of said region.

10. An X-ray control method according to claim 1, wherein said step of arithmetically determining said mean value M' includes:
- a step of eliminating glare scatter components existing in said reference image; and
- a step of arithmetically determining said mean value M' on the basis of said reference image from which said glare scatter components have been eliminated.

11. An X-ray control method according to claim 1, wherein said step of arithmetically determining said mean value M' includes:
- a step of setting a concerned part of said object under inspection which is to undergo an X-ray fluoroscopy and an X-ray radiography; and
- a step of determining said weighting function on the basis of said concerned part.

12. An X-ray control method according to claim 1, wherein said step of arithmetically determining said mean value M' includes:
- a step of setting for said reference image a region in which said mean value M' is to be arithmetically determined; and
- a step of arithmetically determining said mean value M' for said region.

13. An X-ray control method according to claim 12, wherein said step of setting the region for arithmetic determination of said mean value M' includes:
- a step of setting said region on the basis of a concerned part for X-ray radiography.

14. An X-ray control method according to claim 12, wherein said step of setting the region for arithmetic determination of said mean value M' includes:
- a step of setting said region on a region representing simulatively an image pick-up range of said imaging means.

15. An X-ray apparatus, comprising:
- an X-ray tube for generating X-rays to irradiate an object under inspection;
- a unit for controlling conditions for generation of X-rays;
- X-ray irradiation field limiting means for limiting an X-ray irradiation field;
- imaging means for picking up an X-ray image of said object under inspection;
- means for arithmetically determining a mean value M' of a weighted histogram obtained by multiplying a histogram representing a distribution of numbers of data corresponding to image intensities in a reference image which is an image obtained from an output signal of said imaging means and a weighting function having a variable dependent on said image intensities; and
- means for controlling output power of said X-ray tube so that said mean value M' approaches a mean value M of said weighting function.

16. An X-ray apparatus according to claim 15, wherein said means for arithmetically determining said mean value M' includes:
- means for selecting said reference image from a fluoroscopic image.

17. An X-ray apparatus according to claim 15, wherein said means for arithmetically determining said mean value M' includes:
- means for selecting said reference image from an X-ray image picked up through a preliminary X-ray radiography performed in precedence to X-ray radiography on X-ray conditions which are weaker than X-ray conditions for the X-ray radiography.

18. An X-ray apparatus according to claim 17, wherein said means for controlling the output power of said X-ray tube includes:
- means for performing control so that a tube voltage of said X-ray tube and said X-ray irradiation field remain same in both the preliminary X-ray radiography and the X-ray radiography.

19. An X-ray apparatus according to claim 15, wherein said means for arithmetically determining said mean value M' includes:
- means for selecting a probability distribution function as said weighting function; and
- means for setting a mean value of said probability distribution function and a standard deviation of said probability distribution function, as functional parameters of said weighting function.

20. An X-ray apparatus according to claim 19, wherein said means for selecting said probability function selects a normal distribution function or an $\chi^2$-distribution having a degree freedom not smaller than three or a t-distribution, as said probability distribution function.

21. An X-ray apparatus according to claim 15, wherein said means for arithmetically determining said mean value M' includes:
- means for decreasing a number of pixels of said reference image relative to a number of pixels of an X-ray image in an X-ray fluoroscopy or in a preliminary X-ray radiography; and
- means for arithmetically determining said mean value M' on the basis of the reference image having the decreased number of pixels.

22. An X-ray apparatus according to claim 15, wherein said means for arithmetically determining said mean value M' includes:
- means for detecting a region in which halation occurs in said reference image;
- means for performing computation of intensities of individual pixels within said region, on the basis of a control value for said X-ray tube, thickness of said object under inspection and a control value for said imaging means in the state where the halation is taking place;

means for performing replacement of the intensities of the pixels within said region by the intensities of the pixels as determined by said computation; and means for arithmetically determining said mean value M' on the basis of a reference image resulting from said replacement.

23. An X-ray apparatus according to claim 22, wherein said thickness of said object under inspection corresponding to said region is determined on the basis of extent of said region.

24. An X-ray apparatus according to claim 15, wherein said means for arithmetically determining said mean value M' includes:

means for eliminating glare scatter components existing in said reference image; and means for arithmetically determining said mean value M' on the basis of said reference image from which said glare scatter components have been eliminated.

25. An X-ray apparatus according to claim 15, wherein said means for arithmetically determining said mean value M' includes:

means for setting a concerned part of said object under inspection which is to undergo an X-ray fluoroscopy and an X-ray radiography; and means for determining said weighting function on the basis of said concerned part.

26. An X-ray apparatus according to claim 25, wherein said means for arithmetically determining said weighting function includes:

means for setting values of functional parameters of said weighting function.

27. An X-ray apparatus according to claim 15, wherein said means for arithmetically determining said mean value M' includes:

means for setting for said reference image a region in which said mean value M' is to be arithmetically determined; and means for arithmetically determining said mean value M' on the basis of said region.

28. An X-ray apparatus according to claim 27, wherein said means for arithmetically determining said mean value M' includes:

means for setting said region for arithmetic determination of said mean value M' on the basis of a concerned part for an X-ray radiography.

29. An X-ray apparatus according to claim 27, wherein said means for arithmetically determining said mean value M' includes:

a plurality of touch sensors for determining on/off states at positions corresponding to subregions generated by dividing a region representing simulatively an image pick-up range of said imaging means;

means for setting as a concerned region of said reference image a picked-up region corresponding to a region in which said touch sensors are in on-state; and means for arithmetically determining said mean value M' on the basis of said concerned region.

30. An X-ray apparatus, comprising:

an X-ray tube for generating X-rays to irradiate an object under inspection;

an X-ray control unit for controlling conditions for generation of X-rays;

an imaging device for picking up an X-ray image of said object under inspection;

a halation correcting module configured so that when halation is taking place in a first X-ray image obtained by an output signal of said imaging device, said halation correcting module provides a second X-ray image corrected by determining normal image intensity in a region in which the halation is taking place in said first X-ray image, on the basis of size of said region, a control value for the X-ray tube, thickness information of said object under inspection and a control value for said imaging device;

a module for setting a concerned region for said second X-ray image;

a module for setting a weighting function for imparting weight to image data in dependence on said concerned region;

a module for determining a weighted histogram by multiplying a histogram representing a distribution of numbers of data corresponding to image intensities and said weighting function for image data of said concerned region, to thereby determine a mean value M' of said weighted histogram; and a module for setting control data for said X-ray control unit so that said mean value M' approaches a mean value M of said weighting function.

31. An X-ray apparatus according to claim 30, further comprising:

a glare correcting module for performing glare correction for an output image of said halation correcting module.

32. An X-ray apparatus according to claim 30, wherein said module for setting said concerned region includes:

a module for selecting a region lying within both said concerned region and an X-ray irradiation field, in accordance with a concerned part for X-ray radiography.

33. An X-ray apparatus according to claim 30, wherein said module for setting the weighting function includes:

a module for setting values of functional parameters of said weighting function, in dependence on the concerned part for X-ray radiography.

* * * * *